(12) United States Patent
Buchheit (10) Patent No.: US 8,954,030 B1
(45) Date of Patent: *Feb. 10, 2015

(54) SAFETY FEATURE TO DISABLE AN ELECTRONIC DEVICE WHEN A WIRELESS IMPLANTABLE MEDICAL DEVICE (IMD) IS PROXIMATE

(71) Applicant: Brian K. Buchheit, Davie, FL (US)

(72) Inventor: Brian K. Buchheit, Davie, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/277,893

(22) Filed: May 15, 2014

Related U.S. Application Data (63) Continuation of application No. 13/568,541, filed on Aug. 7, 2012, now Pat. No. 8,761,717.

(51) Int. Cl.
*H04M 11/04* (2006.01)
*A61N 1/08* (2006.01)
*A61N 1/37* (2006.01)
(Continued)

(52) U.S. Cl.
CPC ......... *A61N 1/3718* (2013.01); *A61M 5/14276* (2013.01); *A61N 1/37258* (2013.01); *A61M 2005/14264* (2013.01)
USPC ........... 455/404.1; 455/41.2; 455/88; 607/30; 607/60

(58) Field of Classification Search
CPC ......... A61N 1/37; A61N 1/3925; A61N 1/08; H04M 11/04
USPC ........... 455/404.1, 41.2, 88, 41.1, 421, 422.1, 455/521, 66.1, 556.1, 557; 607/30, 60, 607/31–32, 59
See application file for complete search history.

(56) References Cited

U.S. PATENT DOCUMENTS

| | | | |
|---|---|---|---|
| 3,692,027 | A | 9/1972 | Ellinwood |
| 4,003,379 | A | 1/1977 | Ellinwood |
| 4,146,029 | A | 3/1979 | Ellinwood |

(Continued)

FOREIGN PATENT DOCUMENTS

| | | |
|---|---|---|
| WO | 0149364 | 7/2001 |
| WO | 02060529 A2 | 8/2002 |

(Continued)

OTHER PUBLICATIONS

U.S. Appl. No. 12/368,385, filed Aug. 12, 2010, Aghassian.

(Continued)

*Primary Examiner* — Pablo Tran
(74) *Attorney, Agent, or Firm* — Patents on Demand P.A.; Brian K. Buchheit; Scott M. Garrett (57) ABSTRACT

A communication pathway is established between an implanted medical device (IMD) and a proximate electronic device. Performance of one or more functions by the electronic device is known to have a potential to cause at least one adverse effect on the implanted medical device. The implanted medical device can wirelessly conveying a message over the communication pathway to the electronic device detailing an existence of the implanted medical device (IMD) within wireless communication range of the electronic device and detailing a safety requirement or operational data specific to the implanted medical device. The conveyance of the message from the implanted medical device can place the proximate electronic device on notice to minimize the adverse effects on the implanted medical device resulting from executing the one or more functions.

28 Claims, 6 Drawing Sheets

(51) Int. Cl.
*A61M 5/142* (2006.01)
*A61N 1/372* (2006.01)

(56) References Cited

U.S. PATENT DOCUMENTS

| | | |
|---|---|---|
| 4,281,664 A | 8/1981 | Duggan |
| 4,299,220 A | 11/1981 | Dorman |
| 4,360,125 A | 11/1982 | Martindale et al. |
| 4,544,371 A | 10/1985 | Dormandy et al. |
| 4,556,063 A | 12/1985 | Thompson et al. |
| 4,635,639 A | 1/1987 | Hakala et al. |
| 4,871,351 A | 10/1989 | Feingold |
| 4,897,987 A | 2/1990 | Spalla |
| 4,944,299 A | 7/1990 | Silvian |
| 4,987,897 A | 1/1991 | Funke |
| 5,040,533 A | 8/1991 | Fearnot |
| 5,041,107 A | 8/1991 | Heil |
| 5,042,497 A | 8/1991 | Shapland |
| 5,058,581 A | 10/1991 | Silvian |
| 5,087,243 A | 2/1992 | Avitali |
| 5,113,859 A | 5/1992 | Funke |
| 5,113,869 A | 5/1992 | Nappholz et al. |
| 5,127,404 A | 7/1992 | Wyborny et al. |
| 5,190,035 A | 3/1993 | Salo et al. |
| 5,220,917 A | 6/1993 | Cammilli et al. |
| 5,269,301 A | 12/1993 | Cohen |
| 5,305,745 A | 4/1994 | Zacouto |
| 5,342,408 A | 8/1994 | deCoriolis et al. |
| 5,368,028 A | 11/1994 | Palti |
| 5,416,695 A | 5/1995 | Stutman et al. |
| 5,456,692 A | 10/1995 | Smith et al. |
| 5,460,605 A | 10/1995 | Tuttle et al. |
| 5,496,360 A | 3/1996 | Hoffmann et al. |
| 5,549,115 A | 8/1996 | Morgan et al. |
| 5,549,659 A | 8/1996 | Johansen et al. |
| 5,551,953 A | 9/1996 | Lattin |
| 5,556,421 A | 9/1996 | Prutchi |
| 5,562,713 A | 10/1996 | Silvian |
| 5,579,876 A | 12/1996 | Adrian et al. |
| 5,586,556 A | 12/1996 | Spivey et al. |
| 5,593,426 A | 1/1997 | Morgan et al. |
| 5,607,418 A | 3/1997 | Arzbaecher |
| 5,674,252 A | 10/1997 | Morgan et al. |
| 5,680,864 A | 10/1997 | Morgan et al. |
| 5,683,423 A | 11/1997 | Post |
| 5,690,682 A | 11/1997 | Buscemi et al. |
| 5,693,075 A | 12/1997 | Plicchi et al. |
| 5,710,551 A | 1/1998 | Ridgeway |
| 5,720,770 A | 2/1998 | Nappholz et al. |
| 5,730,125 A | 3/1998 | Prutchi et al. |
| 5,749,902 A | 5/1998 | Olson et al. |
| 5,749,913 A | 5/1998 | Cole |
| 5,782,878 A | 7/1998 | Morgan et al. |
| 5,787,155 A | 7/1998 | Luna |
| 5,817,131 A | 10/1998 | Elsberry et al. |
| 5,836,935 A | 11/1998 | Ashton et al. |
| 5,836,993 A | 11/1998 | Cole |
| 5,891,046 A | 4/1999 | Cyrus et al. |
| 5,891,049 A | 4/1999 | Cyrus et al. |
| 5,893,881 A | 4/1999 | Elsberry et al. |
| 5,899,866 A | 5/1999 | Cyrus et al. |
| 5,899,928 A | 5/1999 | Sholder et al. |
| 5,921,938 A | 7/1999 | Aoyama et al. |
| 5,925,066 A | 7/1999 | Kroll et al. |
| 5,951,485 A | 9/1999 | Cyrus et al. |
| 5,999,493 A | 12/1999 | Olson |
| 6,041,257 A | 3/2000 | MacDuff |
| 6,045,513 A | 4/2000 | Stone et al. |
| 6,047,207 A | 4/2000 | MacDuff et al. |
| 6,057,758 A | 5/2000 | Dempsey et al. |
| 6,090,056 A | 7/2000 | Bystrom et al. |
| 6,115,636 A | 9/2000 | Ryan |
| 6,141,584 A | 10/2000 | Rockwell et al. |
| 6,141,588 A | 10/2000 | Cox |
| 6,150,951 A | 11/2000 | Olejniczak |
| 6,201,992 B1 | 3/2001 | Freeman |
| 6,250,309 B1 | 6/2001 | Krichen et al. |
| 6,292,698 B1 | 9/2001 | Duffin et al. |
| 6,301,502 B1 | 10/2001 | Owen et al. |
| 6,304,780 B1 | 10/2001 | Owen et al. |
| 6,321,113 B1 | 11/2001 | Parker et al. |
| 6,374,138 B1 | 4/2002 | Owen et al. |
| 6,405,083 B1 | 6/2002 | Rockwell et al. |
| 6,411,840 B1 | 6/2002 | Bardy |
| 6,418,346 B1 | 7/2002 | Nelson et al. |
| 6,427,083 B1 | 7/2002 | Owen et al. |
| 6,438,417 B1 | 8/2002 | Rockwell et al. |
| 6,442,433 B1 | 8/2002 | Linberg |
| 6,453,195 B1 | 9/2002 | Thompson |
| 6,471,645 B1 | 10/2002 | Warkentin et al. |
| 6,477,424 B1 | 11/2002 | Thompson et al. |
| 6,480,745 B2 | 11/2002 | Nelson et al. |
| 6,493,581 B2 | 12/2002 | Russell |
| 6,510,345 B1 * | 1/2003 | Van Bentem .................. 607/60 |
| 6,516,227 B1 | 2/2003 | Meadows et al. |
| 6,574,511 B2 | 6/2003 | Lee |
| 6,594,634 B1 | 7/2003 | Hampton et al. |
| 6,597,948 B1 | 7/2003 | Rockwell et al. |
| 6,599,250 B2 | 7/2003 | Webb et al. |
| 6,668,192 B1 | 12/2003 | Parker et al. |
| 6,694,186 B2 | 2/2004 | Bardy |
| 6,704,595 B2 | 3/2004 | Bardy |
| 6,754,527 B2 * | 6/2004 | Stroebel et al. ............... 607/5 |
| 6,826,425 B2 | 11/2004 | Bardy |
| 6,892,092 B2 | 5/2005 | Palreddy et al. |
| 6,904,312 B2 | 6/2005 | Bardy |
| 6,909,916 B2 | 6/2005 | Spinelli et al. |
| 7,072,711 B2 | 7/2006 | Girouard et al. |
| 7,089,055 B2 | 8/2006 | Cates et al. |
| 7,130,695 B2 | 10/2006 | Schaldach |
| 7,167,755 B2 | 1/2007 | Seeberger et al. |
| 7,177,698 B2 | 2/2007 | Klosterman et al. |
| 7,201,733 B2 | 4/2007 | Scheiner et al. |
| 7,236,821 B2 | 6/2007 | Cates et al. |
| 7,320,675 B2 | 1/2008 | Pastore et al. |
| 7,340,303 B2 | 3/2008 | Zhu |
| 7,369,890 B2 | 5/2008 | Lovett |
| 7,425,210 B2 | 9/2008 | Sweeney et al. |
| 7,526,335 B2 | 4/2009 | Ferek-Petric |
| 7,567,841 B2 | 7/2009 | Chan |
| 7,621,906 B2 | 11/2009 | Pastore et al. |
| 7,627,373 B2 | 12/2009 | Girouard et al. |
| 7,729,761 B2 | 6/2010 | Girouard et al. |
| 7,764,995 B2 | 7/2010 | Girouard et al. |
| 7,787,958 B2 | 8/2010 | Stevenson |
| 7,828,711 B2 | 11/2010 | Ross et al. |
| 7,840,263 B2 | 11/2010 | Girouard et al. |
| 7,937,148 B2 | 5/2011 | Jacobson |
| 7,945,333 B2 | 5/2011 | Jacobson |
| 7,976,534 B2 * | 7/2011 | Gerber et al. .............. 604/891.1 |
| 7,978,064 B2 | 7/2011 | Zdeblick |
| 7,981,065 B2 | 7/2011 | Westlund et al. |
| 8,010,209 B2 | 8/2011 | Jacobson |
| 8,016,783 B2 | 9/2011 | Pastore et al. |
| 8,036,748 B2 | 10/2011 | ZDeblick |
| 8,054,140 B2 | 11/2011 | Fleming |
| 8,055,334 B2 | 11/2011 | Savage et al. |
| 8,060,219 B2 | 11/2011 | Ross et al. |
| 8,114,021 B2 | 2/2012 | Robertson et al. |
| 8,634,927 B2 * | 1/2014 | Olson et al. .................. 607/60 |
| 8,649,757 B2 * | 2/2014 | Roberts et al. ............. 455/404.1 |
| 2002/0029002 A1 | 3/2002 | Bardy |
| 2002/0087113 A1 | 7/2002 | Hartlaub |
| 2002/0099303 A1 | 7/2002 | Bardy |
| 2002/0099328 A1 | 7/2002 | Scheiner et al. |
| 2002/0123778 A1 | 9/2002 | Linberg |
| 2002/0169584 A1 | 11/2002 | Fu et al. |
| 2002/0173727 A1 | 11/2002 | Bardy |
| 2002/0193846 A1 | 12/2002 | Pool et al. |
| 2003/0025602 A1 | 2/2003 | Medema et al. |
| 2003/0058097 A1 | 3/2003 | Saltzstein et al. |
| 2003/0109904 A1 | 6/2003 | Silver et al. |
| 2004/0088027 A1 | 5/2004 | Burnes et al. |
| 2004/0138648 A1 | 7/2004 | Sweeny et al. |

(56) References Cited

U.S. PATENT DOCUMENTS

| | | |
|---|---|---|
| 2004/0152993 A1 | 8/2004 | Bardy |
| 2004/0199212 A1 | 10/2004 | Fischell et al. |
| 2004/0204744 A1 | 10/2004 | Penner et al. |
| 2004/0225337 A1 | 11/2004 | Housworth et al. |
| 2005/0027331 A1 | 2/2005 | Bardy |
| 2005/0144038 A1 | 6/2005 | Tamblyn et al. |
| 2006/0085040 A1 | 4/2006 | Vandanacker |
| 2006/0212096 A1 | 9/2006 | Stevenson |
| 2007/0060980 A1 | 3/2007 | Strother et al. |
| 2007/0112398 A1 | 5/2007 | Stevenson et al. |
| 2008/0027500 A1 | 1/2008 | Chen |
| 2008/0051668 A1 | 2/2008 | Bardy |
| 2009/0112291 A1 | 4/2009 | Wahlstrand et al. |
| 2009/0118796 A1 | 5/2009 | Chen |
| 2011/0004275 A1 | 1/2011 | Carbunaru et al. |
| 2011/0160808 A1* | 6/2011 | Lyden et al. .............. 607/63 |
| 2012/0003595 A1 | 1/2012 | Goh et al. |

FOREIGN PATENT DOCUMENTS

| | | |
|---|---|---|
| WO | 02074386 | 9/2002 |
| WO | 2005009514 | 2/2005 |

OTHER PUBLICATIONS

U.S. Appl. No. 12/471,626, filed Dec. 2, 2010, Ozawa.
U.S. Appl. No. 12/476,523, filed Dec. 2, 2010, Aghassian.
U.S. Appl. No. 12/484,052, filed Dec. 16, 2010, Aghassian.
U.S. Appl. No. 11/780,369, filed Jan. 22, 2009, Dronov.

* cited by examiner

SAFETY FEATURE TO DISABLE AN ELECTRONIC DEVICE WHEN A WIRELESS IMPLANTABLE MEDICAL DEVICE (IMD) IS PROXIMATE

CROSS REFERENCE TO RELATED APPLICATIONS

This application claims priority to application Ser. No. 13/568,541, which was filed on 7 Aug., 2012, and is incorporated herein in its entirety.

BACKGROUND

The present invention relates to the field of medical devices and, more particularly, to a safety feature for implanted medical devices (IMDs).

Implantable medical devices (IMDs) are a subset of medical devices that are partially or totally inserted into a human body or natural orifice (or is used to replace an epithelial surface or surface of the eye) and are expected to stay in place for over thirty days. Examples of IMDs include, but are not limited to: cardiac defibrillators (sometimes referred to as implantable cardioverter-defibrillator or ICDs), pacemakers, deep brain neurostimulators, gastric stimulators, foot drop implants, cochlear implants, insulin pumps, and the like. Some IMDs include wireless communication capabilities for communicating with various electronic devices like medical monitors or programmers.

Implantable medical devices (IMDs) extend the life and/or enhance the quality of life of millions of people. Many electronic devices encountered in our daily lives have the potential to interfere with the operation of an IMD. Often, the implantee, the person in whom the IMD is implanted, or an operator of the electronic device is unaware of the potentially dangerous interaction, particularly in an emergency situation where the implantee is unable to provide information about their health and IMD.

In the attempt to circumvent this problem, some IMDs have been designed to mitigate detected electromagnetic or radio frequency interference either by using materials that provide better protection or adjusting the operation of the IMD. While this type of approach addresses the problem, the IMD, a resource-constrained device, must be able to accommodate the additional space and power consumption to support the additional components required for mitigation. Further, these approaches are limited to only those devices that emit electromagnetic or radio waves. For example, this type of IMD would not prohibit an automated drug delivery system from administering pain medication that is known to adversely interact with the medication provided by a patient's implanted drug pump.

DETAILED DESCRIPTION

This disclosure provides for a solution for mitigating the adverse effects of functions performed by an electronic device upon a proximately-located implanted medical device (IMD). An IMD safety control can be coupled with the electronic device in order to disable the performance of the functions that can have an adverse effect upon operation of the implanted medical device or a treatment provided by the implanted medical device when the implanted medical device is detected within an effective proximity of the electronic device. An operator of the electronic device can be notified of the presence of the implanted medical device and resolution requested. The functions can be enabled upon receipt of the resolution. In one embodiment, bidirectional communications can occur between the proximate electronic device and the IMD, which enable either/both devices to change their state and/or trigger functions to ensure maximum safety. For example, an IMD device can immediately go into a "safe" mode right before a cardiac defibrillator emits a charge to a wearer of an IMD, and the IMD can immediately go back "online" out of the "safe" mode after the charge to ensure proper regulation of the wearer's body (such as the wearer's heart) post-charge. No known solution exists for this problem, where no automatic adjustments are made between an IMD and proximate electronic device(s) to ensure that these electronic devices pose no harm to an IMD. This even applies to devices specifically designed for patient care (such as those within an ambulance or hospital) as well as common environmental devices (like microwave ovens, security detectors, etc.). This lack of automatic safeguard results in severe physical ramifications to IMD wearers, when oversights occur (such as not adjusting an MRI to ensure that an IMD wearer is unharmed by the MRI procedure).

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list)

of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 1:
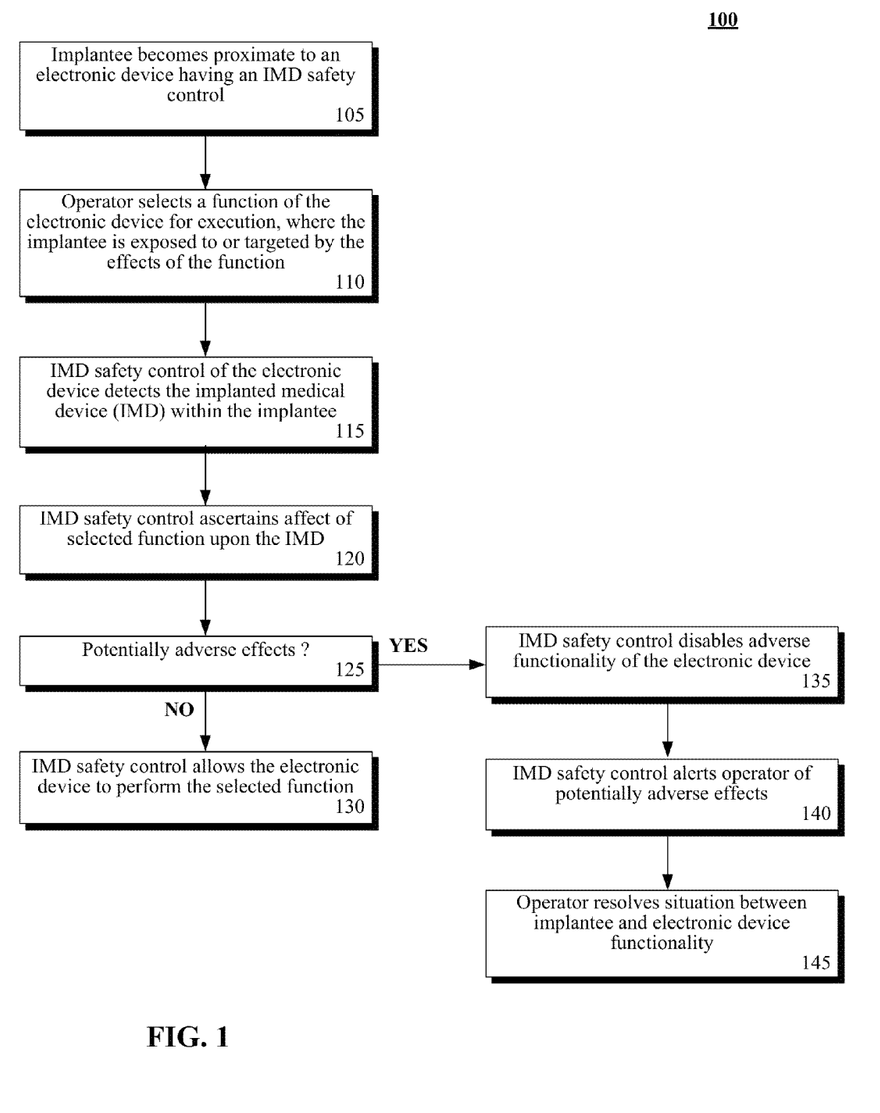
FIG. 1 is a flowchart of a method describing the general use of an electronic device having an implantable medical device (IMD) safety control in accordance with an embodiment of the disclosure.

Referring to the figures, FIG. 1 is a flowchart of a method 100 describing the general use of an electronic device having an implantable medical device (IMD) safety control in accordance with an embodiment of the disclosure. The general purpose of the IMD safety control can be to minimize the occurrence of potentially adverse interactions caused by functions of the electronic device and the operation of the IMD.

Method 100 can begin in step 105 where an implantee can become proximate to an electronic device having an IMD safety control. Step 105 can encompass movement on the part of the implantee (e.g., a person walking), movement on the part of the electronic device (e.g., a mobile device or a device transported upon or within a carrier), or simultaneous movement of both.

An operator of the electronic device can select a function for execution that targets or exposes the implantee to the effects of the selected function in step 110. For example, the functions of a medical monitoring device target a single person, but not others nearby, while the radiation from a microwave oven affects all in limited area.

In step 115, the IMD safety control of the electronic device can detect the IMD within the implantee. Step 115 can be performed in a variety of ways known in the art. The IMD safety control can ascertain the effect of the selected function upon the IMD in step 120. Step 120 can utilize data from a variety of sources (e.g., local and network) depending upon the specific implementation and communicative environment.

In step 125, the IMD safety control can determine if its function will have any potentially adverse effects, either directly to the IMD (e.g., electrical interference) or indirectly via physiological changes to the implantee (e.g., medication delivered). When it is determined that the function will have no potentially adverse effects, the IMD safety control can allow the electronic device to perform the selected function in step 130.

When the function has the potential to adversely affect the IMD or implantee, step 135 can be performed where the IMD safety control can disable the adverse functionality of the electronic device. The IMD safety control can then alert the operator of the electronic device to the potentially adverse effects in step 140.

In step 145, the operator can resolve the situation between the implantee and electronic device functionality. For example, the operator can select a different function of the electronic device, ask the implantee to remove themselves from the area affected by the function, utilize a different device or method, and the like, depending on the function being performed.

It should be emphasized that an electronic device without the IMD safety control would perform the selected function, regardless; potentially harming the implantee and/or the IMD. Further, the IMD safety control can be used with electronic devices that do not emit electronic or radiological interference but whose functions affect the implantee, and the IMD, by extension, like a drug delivery system.

Figure 2:
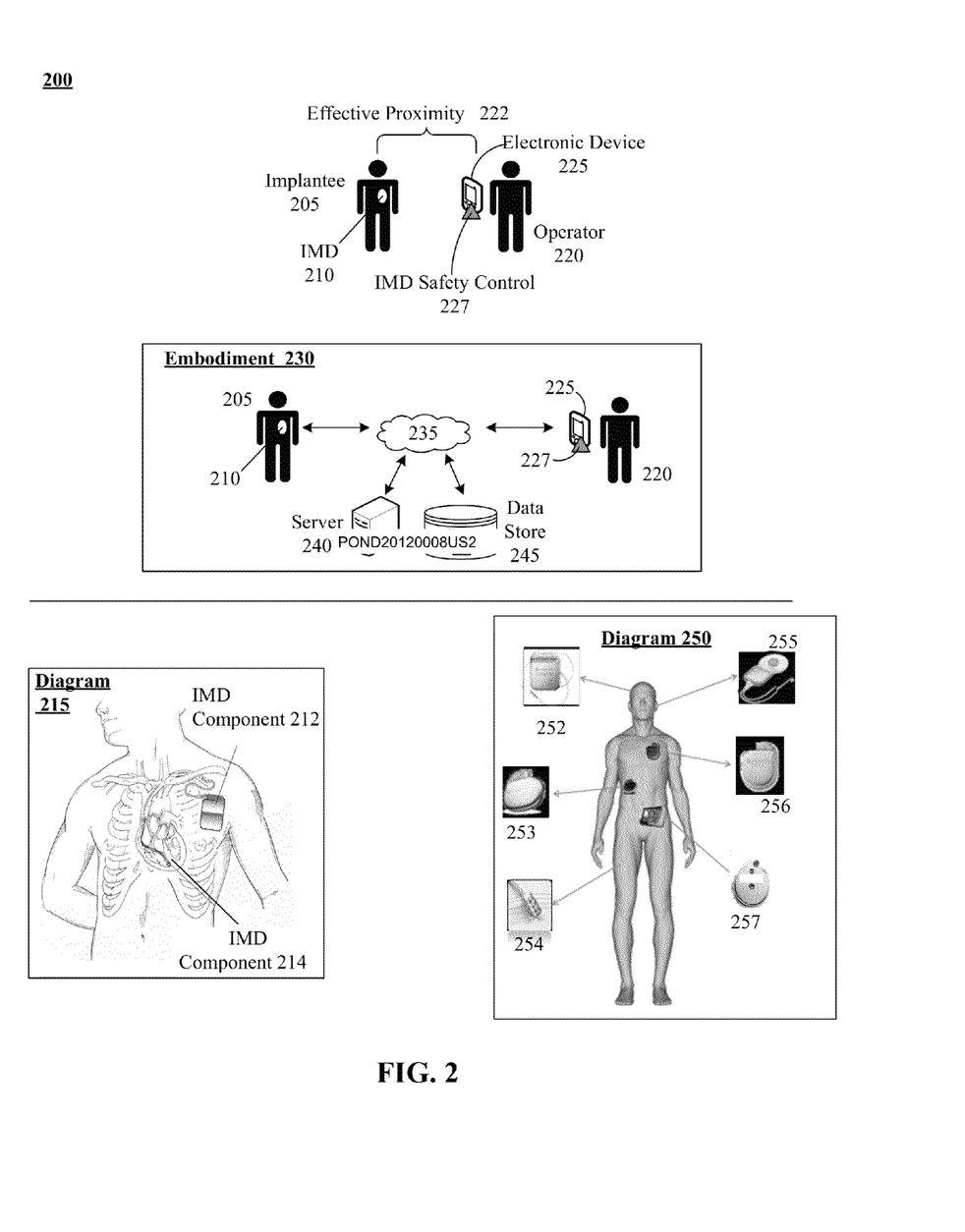
FIG. 2 is a schematic diagram illustrating an implantee having an implanted medical device (IMD) within the effective proximity of an electronic device equipped with an IMD safety control in accordance with an embodiment of the disclosure.

FIG. 2 is a schematic diagram 200 illustrating an implantee 205 having an implanted medical device (IMD) 210 within the effective proximity 222 of an electronic device 225 equipped with an IMD safety control 227 in accordance with an embodiment of the disclosure. The steps of method 100 can be performed within the context of illustration 200.

The IMD 210 can include wireless communication abilities. As shown in embodiment 230, the IMD 210 can wirelessly communicate via a network 235 with one or more devices connected to the network 235. The devices can include a server 240, a network data store 245, and/or an electronic device 225 controlled by an operator 220. Communications over the network 235 with the IMD 210 can be unidirectional or bidirectional, depending on implementation specifics. Additionally, communications can be active, semi-active, or passive ones from the IMD 210 perspective, in various embodiments. The electronic device 225 can receive the IMD information directly, indirectly (i.e., through server 240 or data store 245), or both depending on the specific embodiment of the disclosure.

As used herein, a medical device can be a manufactured product used to cope with human disease, care for human injuries, meet human anatomical needs, maintain human anatomical needs, maintain or monitor human physiological functions, support or sustain human life, control human conception, or examine specimens or from human bodies. An implanted medical device or IMD 210 can be a medical device that is partially or totally inserted into the human body or natural orifice and is expected to stay in there for thirty days or more. Additionally, IMD 210 can be a medical device used to replace an epithelial surface or the surface of the eye that is expected to stay in place for thirty days or more. Surgical or medical procedures can be used to insert or apply IMDs 210 and surgical or medical procedures can be used to remove IMDs 210.

IMD 210 can be an active or passive device. An active IMD 210 can be an implanted medical device that uses electrical energy or other power to make it function. Devices that are powered by the human body or by gravity are not generally considered active IMDs by this definition. Human body powered and/or gravity powered IMDs 210 are to be considered passive IMDs 210, which are included within the scope of embodiments of the disclosure.

Diagram 250 visually depicts a non-exclusive listing of IMDs 210 able to be implanted in the human body of implantee 205. These IMDs 210 can include neurostimulators 252 (e.g., cortical stimulators, deep brain stimulators, spinal cord stimulators and vagus nerve stimulators, sacral nerve stimulation, etc.), gastric stimulators 253, foot drop and other skeletal implants 254, cochlear implants 255, cardiac implants 256 (e.g., cardioverter-defibrillator, cardiac resynchronization device, cardiac defibrillators, pacemakers, etc.), medication pumps 257 (e.g., insulin pumps, morphine pumps, etc.), bone fusion stimulators, and the like.

The IMD 210 can be a single, discrete device implanted in the implantee 205, or can consist of two or more components. For example, diagram 215 showing the body of implantee 205 illustrates that IMD 210 can include two different components; IMD component 212 and IMD component 214. More specifically, an ICD is shown, where component 212 is an automatic implantable cardioverter defibrillator and component 214 is an electrode inserted into the heart of implantee 205.

Many existing standards exist that provide definitions and standards for IMDs 210, which are to be selectively considered as applicable to the present disclosure to the extent that they define IMDs 210 and to the extent these definitions are consistent with embodiments of the disclosure. To elaborate, the International Organization for Standards (ISO) has established TC 150 for implants for surgery: more specifically TC150/SC1 (subcommittee for materials), TC150/SC2 (subcommittee for cardiovascular implants and extracorporeal systems), TC 150/SC3 (subcommittee for Neurosurgical implants), TC 150/SC4 (subcommittee for bone and joint replacements), TC 150/SC5 (subcommittee for Osteosynthesis and spinal devices), TC 150/SC6 (subcommittee for active implants), and TC 150/SC7 (subcommittee for tissue-engineered medical products). Documents for these subcommittees and definitions contained therein are to be considered applicable for definitions of IMD 210, as used and defined in embodiments of the disclosure. For example, ISO 13485: 2003 "Medical Devices—quality management systems—requirements for regulator purposes" is applicable to embodiments of the disclosure for IMDs 210. Appreciably these standards are not to be construed as limiting the scope of the disclosure, but are useful for providing additional definitional material and specifics not expressly detailed herein, but which are to be considered as having been contemplated by the disclosure.

The electronic device 225 can include components whose functionality impacts the physiology of the implantee 205 and/or operation of the IMD 210. As shown in diagram 230, the electronic device 225 can be of a portable or hand-held nature like a cell phone. The electronic device 225 is not to be construed as limited to portable electronic devices, but can also include devices that are relatively stationary, such as personal computers, microwaves, specialized medical devices, and the like.

The electronic device 225 can be configured to support operation of the IMD safety control 227. The IMD safety control 227 can represent the hardware and/or software components required to detect the IMD 210 of the implantee 205 and prohibit functionality of the electronic device 225 should the functionality pose a danger to the implantee 205 and/or IMD 210, as discussed in method 100.

For example, in one embodiment, the IMD safety control 227 can be a logic circuit built into the electronic device 225; in another embodiment, the IMD safety control 227 can be a software program that interacts with the software that controls operation of the electronic device 225.

In its simplest form, the IMD safety control 227 can be thought of as an automated "kill switch" for the electronic device 225, suspending operation of the electronic device 225 when an IMD 210 is detected within the effective proximity 222. The effective proximity 222 can represent a predefined physical distance that the electronic device 225 is known to adversely affect the operation of an IMD 210.

Embodiment 230 can illustrate a robust implementation of the IMD safety control 227. In embodiment 230, the IMD safety control 227 can communicate with IMD 210, server 240 and/or data store 245 over the network 235 to collect additional information about the implantee 205 and/or IMD 210, as well as data regarding the interaction of the electronic device 225 with IMD 210.

For example, upon detection of the IMD 210, the IMD safety control 227 can establish a communication link to the IMD 210 over the network 235 to acquire basic patient and/or operational data. From the acquired data, the IMD safety control 227 can then obtain safety or interaction information about the specific IMD 210 from a trusted data source like the Web site of the IMD 210 manufacturer or an applicable governing body. Such information can then be used by the IMD safety control 227 to determine if the implantee 205 and/or IMD 210 are at risk for an adverse interaction with the function of the electronic device 225.

As used herein, presented data store 245 can be a physical or virtual storage space configured to store digital information. Data store 245 can be physically implemented within any type of hardware including, but not limited to, a magnetic disk, an optical disk, a semiconductor memory, a digitally encoded plastic memory, a holographic memory, or any other recording medium. Data store 245 can be a stand-alone storage unit as well as a storage unit formed from a plurality of physical devices. Additionally, information can be stored within data store 245 in a variety of manners. For example, information can be stored within a database structure or can be stored within one or more files of a file storage system, where each file may or may not be indexed for information searching purposes. Further, data store 245 can utilize one or more encryption mechanisms to protect stored information from unauthorized access.

Figure 3:
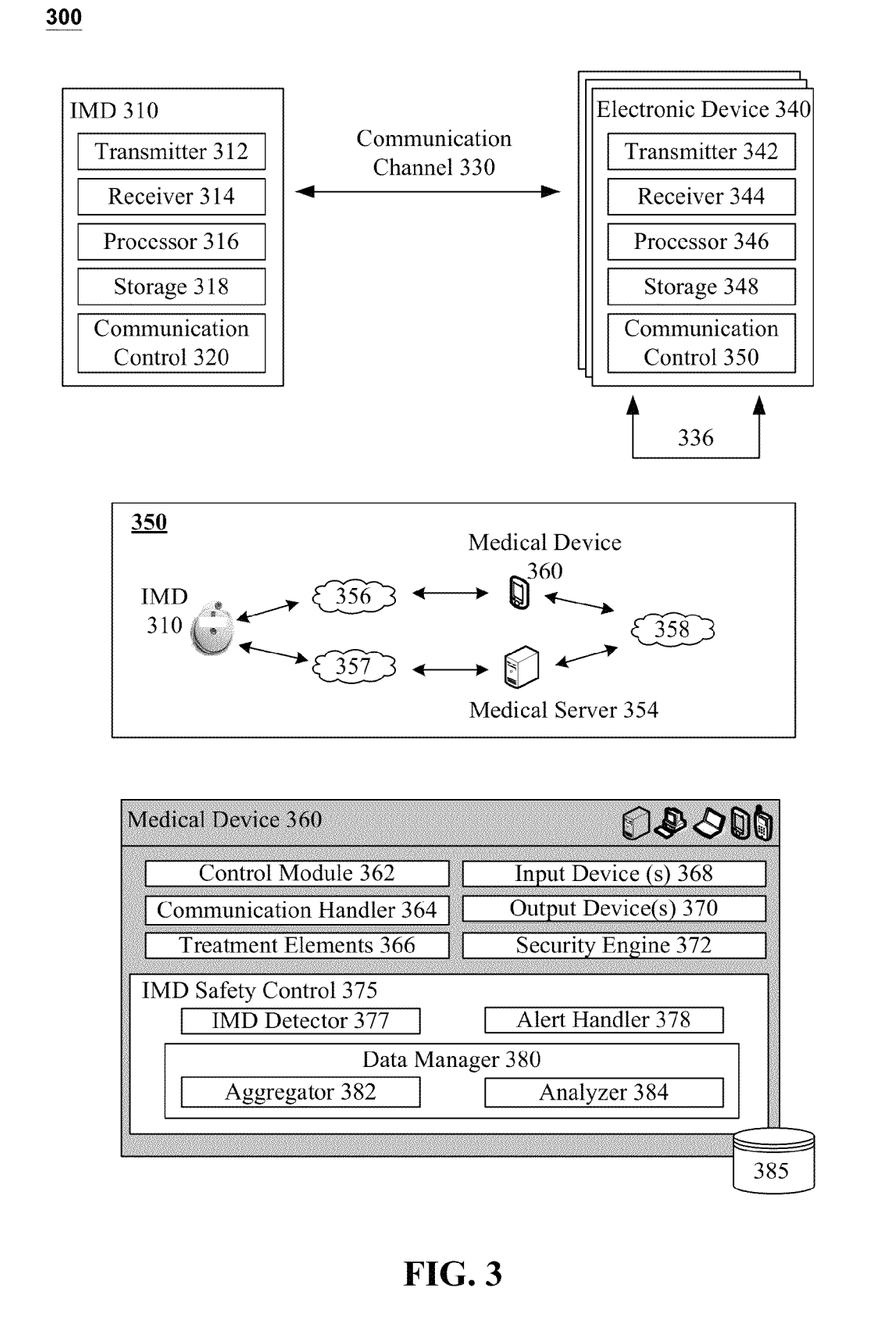
FIG. 3 depicts an exemplary IMD communicatively linked to one or more electronic devices in accordance with an embodiment of the disclosure.

FIG. 3 depicts an exemplary IMD 310 (i.e., one embodiment of IMD 210) communicatively linked to one or more electronic devices 340 in accordance with an embodiment of the disclosure. The IMD 310 can be an active IMD having a transmitter 312, receiver 314 (or both combined as a transceiver), one or more processors 316, storage 318, and communication control 320 circuits/program code.

Each electronic device 340 can be configured to include a transmitter 342, receiver 344, processor 346, storage 348, and communication control 350 circuits/program code. Common examples of electronic devices 340 can include medical devices and devices that emit signal energy (e.g., electromagnetic, x-ray, radio, etc.) waves. The transmitter 312 and/or receiver 314 of IMD 310 can provide for wireless communications.

Communications to/from IMD 310 can occur over one or more communication channels 330. When multiple channels are used, different security measures and requirements can exist for these different communication channels 330. Further, different ones of these channels can be linked to different functions. That is, some protected functions may only be accessed over one channel, information of a particular type may be accessible over one channel and not another, etc. Each of the different communication channels 330 can utilize secure transmission protocols to ensure data conveyed over each is protected during transmission. One or more encryption techniques can be used by one or more of the channels 330.

Any of a variety of cryptography techniques can be used to secure channels 330, such as use of hardware and/or software keys. Hardware based keys can be specifically useful, especially when the utilized keys for the channels 330 are never transported over a network, thus eliminating risks of interception of keys. A public key infrastructure (PKI) can be used to at least partially secure the channels 330 in one embodiment. The channels 330 can also utilize identity-based encryption (IBE), and PKI with an on-line trusted third party (TTP) based techniques. In still another embodiment, biometric based inputs and/or hardware keys unique to an electronic device 340, an implantee, and IMD 310 can be utilized. For example, in one embodiment, a biometric input can be used to additionally secure one of the communication channels 330, which provides an additional level of assurance that a user of the electronic device 340, through which IMD data is provided, is an authorized information recipient.

Use of a short-range broadcast between the IMD 310 and the electronic device 340 is another means of enhancing security when transmitting IMD data. BLUETOOTH, WIRELESS USB, and other protocols (as well as derivatives thereof) exist that have a relatively short broadcasting range (under 10 meters, for example), which can be used for localized communications between IMD 310 and an electronic device 340. Similarly near field communications (NFC) can be used, which typically have a range of six inches or less to ensure that IMD data is conveyed securely between IMD 310 and the electronic device 340. Use of a NFC can be especially useful in embodiments of the disclosure, as power required for data transmissions generally increases with distance and minimizing power of the IMD 310 consumed for transmissions can be essential. When the electronic device 340 is a mobile telephony device or is able to communicate over a mobile telephony network, existing security protocols existing on these devices can be leveraged and enhanced (such as through a double-encryption scheme) to ensure channels 330 are secure.

Diagram 350 illustrates an example configuration of an IMD 310, a medical server 354 (one of the electronic devices 340), and a medical device 360 (another electronic device 340). A set of different networks 356, 357, 358 can interconnect these devices. For example, network 356 can be a near field communication (NFC) or a personal area network. Network 357 can be a mobile telephony network, and network 358 can be an internet protocol (IP) network. In another embodiment, the illustrated networks 356, 357, 358 can be a common network.

Medical device 360 can be an electronic device 340 designed for use in a medical context, such as a monitoring device, a drug delivery system, a scanning device, and the like. In a different embodiment, the electronic device 340 can be a device specifically manufactured/constructed for a different context (e.g., laboratory tasks, manufacturing tasks, etc.). A special purposed device can have unique hardware, electronic boards, firmware, etc., which is not able to be easily modified by software.

As shown in the block diagram, medical device 360 can include components such as a control module 362, communication handler 364, treatment elements 366, input devices 368, output devices 370, security engine 372, the IMD safety control 375, and data store 385.

The control module 362 can represent the elements that control operation of the medical device 360, such as one or more processors, one or more nonvolatile memories, one or more volatile memories, and other such components linked via a bus. The communication handler 364 can include one or more receivers, transmitters, and/or transceivers. The communication handler 364 can enable wired and/or wireless communications of very short range (NFC range), short range (under 10 meters), medium range (WIFI range), and/or long range (cellular or mobile telephony).

The treatment components 366 can represent the elements required by the medical device 360 to perform its designated treatment or function. For example, a drug delivery system would have elements for storing, measuring, and providing the drug to the patient (i.e., subcutaneous, injection, etc.), a defibrillator would have elements for providing an electric shock, and so on.

Input devices 368 can include buttons, dials, a touch pad, a touch screen, a keyboard, a microphone for speech input, a biometric sensor, a camera, an accelerometer, and the like. Output devices 370 can include a display, a speaker, a vibration generator, and the like. The security engine 372 can encrypt/decrypt data, which includes data sent from the IMD device 310. The communication engine 376 can permit the medical device 360 to communicate over one or more of the communication channels 330.

The IMD safety control 375 can include components such as an IMD detector 377, alert handler 378, and data manager 380. The IMD detector 377 can be the components utilized in detecting the presence of IMD 310 in the effective proximity 222. The IMD detector 377 can follow predefined standards in the art for identifying the presence of an IMD 310, such as broadcasting a message on an applicable communication channel 330 to request identification from the IMD 310.

The data manager 380 can utilize an aggregator 382 and analyzer 384 to determine if the function of the medical device 360 has the potential to harm the implantee or IMD 310. The aggregator 382 can be configured to collect pertinent data from trusted data sources, like medical server 354 and data store 385. The analyzer 384 can determine if the operation of the IMD 310 or the health of the implantee could be adversely affected by the function to be performed by the medical device 360.

The data manager 380 can invoke the alert handler 378 when potentially adverse conditions are identified. The alert handler 378 can utilize the output devices 370 to display a message to the operator as well as trigger an audible and/or visual alarm of the medical device 360, when available. Depending upon the specific configuration and capabilities of the medical device 360, the alert handler 378 can also convey a message over one or more networks 356-358 to another electronic device 340 like an emergency page to a doctor or nurse.

The alert handler 378 can also be responsible for interacting with the control module 362 to disable or lock-out one or more treatment elements 366, as well as releasing the treatment elements 366 once resolution of the identified problem has been entered by the operator and/or once the IMD 310 is no longer within the effective proximity 222.

In the embodiment of the IMD safety control 375 shown in medical device 360, the IMD safety control 375 can utilize components of the medical device 360 like the communication handler 364, input devices 368, output devices 370, and elements of the control module 362.

In another contemplated embodiment, the IMD safety control 375 can be an independent device that is coupled with or connected to the medical device 360. In such an embodiment, the IMD safety control 375 can have a separate control module 362 and communication handler 364, interfacing with the medical device 360 to perform input/output and control functionalities.

As used herein, presented storages 318 and 348 and data store 385 can be a physical or virtual storage space configured to store digital information. Storages 318 and 348 and data store 385 can be physically implemented within any type of hardware including, but not limited to, a magnetic disk, an optical disk, a semiconductor memory, a digitally encoded plastic memory, a holographic memory, or any other recording medium. Storages 318 and 348 and/or data store 385 can be formed from a plurality of physical devices. Additionally, information can be stored within storages 318 and 348 and data store 385 in a variety of manners. For example, information can be stored within a database structure or can be stored within one or more files of a file storage system, where each file may or may not be indexed for information searching purposes. Further, storages 318 and 348 and/or data store 385 can utilize one or more encryption mechanisms to protect stored information from unauthorized access.

Figure 4:
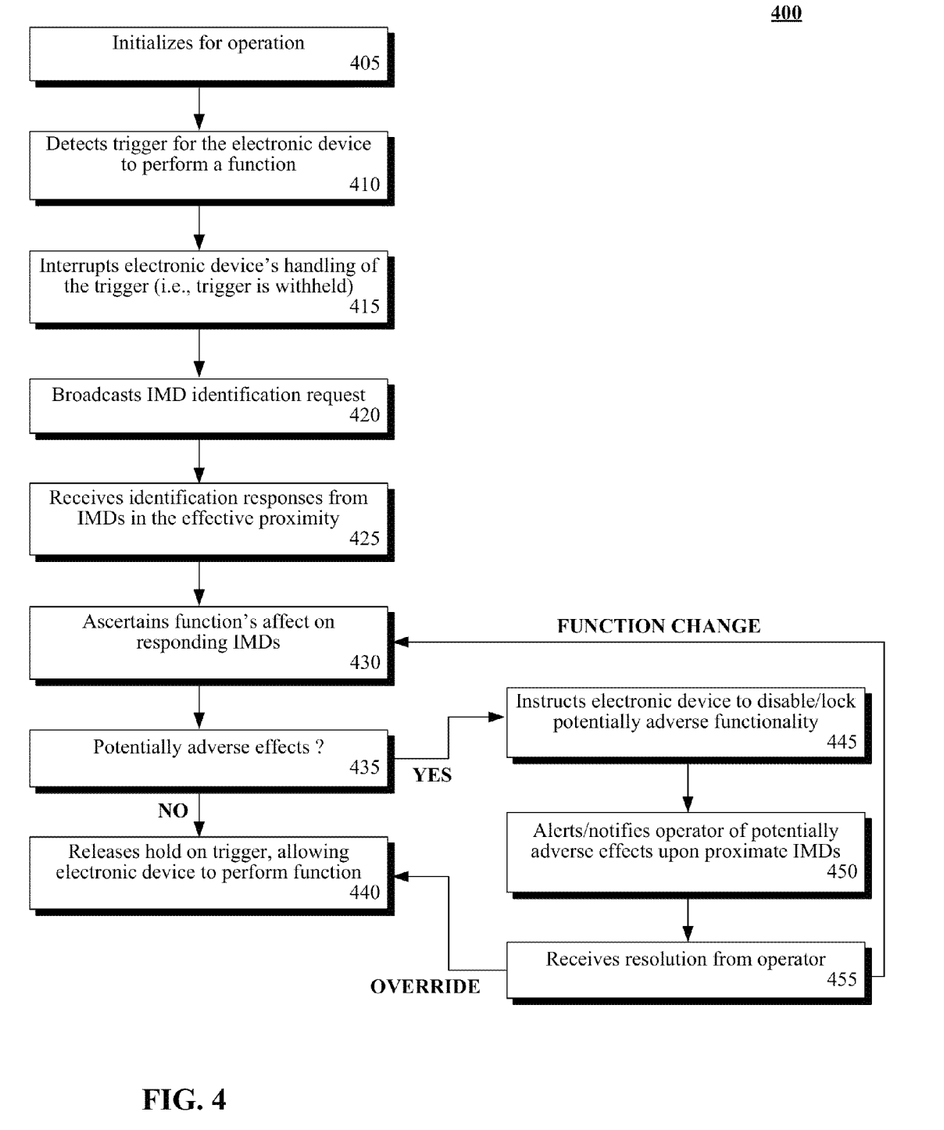
FIG. 4 is a flowchart of a method describing the general operation of the IMD safety control in accordance with an embodiment of the disclosure.

FIG. 4 is a flowchart of a method 400 describing the general operation of the IMD safety control in accordance with an embodiment of the disclosure. Method 400 can begin in step 405, where the IMD safety control can initialize for operation. In step 410, a trigger for the electronic device to perform a function can be detected. Triggers can include function calls, button presses, menu selections, and the like, depending upon the type of electronic device.

The handling of the trigger by the electronic device can be interrupted by the IMD safety control in step 415. For example, processing of the triggering event by the electronic device can be interrupted and the trigger message or command withheld by the IMD safety control.

In step 420, an IMD identification request can be broadcast upon known, applicable communication channels. Identification responses can be received from IMDs in the effective proximity in step 425. Steps 420 and 425 can represent simple IMD detection. The conveyance of requests and responses can occur over a network, which can connect the electronic device to the IMD directly or indirectly.

In step 430, the effect of the triggered function on the responding IMDs can be ascertained. The possibility of the triggered function having a potentially adverse effect upon one or more of the responding IMDs can be determined in step 435.

When it is determined that the triggered function will not have an adverse effect upon the IMD, step 440 can execute where the IMD safety control can release its hold upon the trigger, allowing the electronic device to perform the function. When it is determined that the triggered will have an adverse effect upon the IMD, the IMD safety control can instruct the electronic device to disable or lock the potentially adverse functionality in step 445.

In an alternate embodiment, step 445 can lock the entirety of the electronic device except for select input/output functionality.

In step 450, the operator can be alerted and/or notified of the potentially adverse effects upon the proximate IMDs. Resolution from the operator can then be received in step 455.

When the received resolution is to override the lock-out, method 400 can flow from step 455 to step 440 where the IMD safety control enables the electronic device to perform the triggered function. Override resolution can require additional inputs such as supervisory identification and/or a password. When the received resolution is a change to the triggered function (i.e., a different function is selected or function parameters are selected), method 400 can flow from step 455 to step 430 where the modified function can be assessed for potentially adverse effects upon the IMD.

Another resolution can be for the operator to decide to not use the electronic device for the implantee (i.e., perform the function manually), which is not explicitly shown in method 400. However, such resolution can be handled as a function change where the change is to cancel execution of the function and method 400 can then terminate after step 455.

Figure 5:
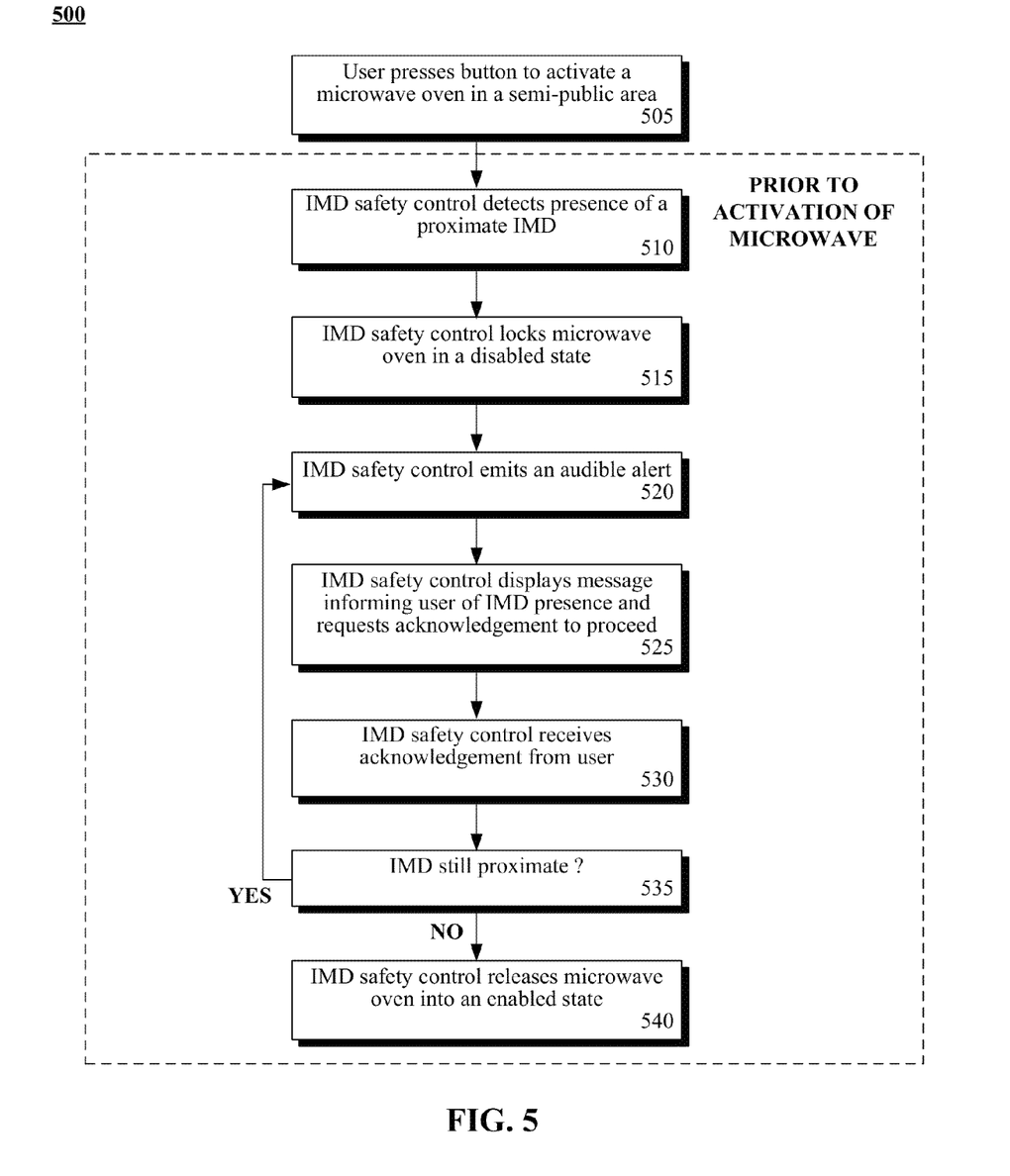
FIG. 5 is a flowchart of a method illustrating operation of a simple IMD safety control within a microwave oven in accordance with an embodiment of the disclosure.

FIG. 5 is a flowchart of a method 500 illustrating operation of a simple IMD safety control within a microwave oven in accordance with an embodiment of the disclosure. Method 500 can begin in step 505, where user presses the button to activate a microwave oven in a semi-public area like a break room or cafeteria (i.e., a location where multiple people are likely to be present).

Prior to the activation of the microwave, the IMD safety control can detect the presence of a proximate IMD in step 510. In step 515, the microwave oven can be locked in a disabled state by the IMD safety control. An audible alert can be emitted by the microwave oven at the command of the IMD safety control in step 520. In step 525, the IMD safety control can display a message in the display area of the microwave oven that informs the user to the presence of a proximate IMD and requests acknowledgement to proceed.

Acknowledgement can be received by the IMD safety control from the user in step 530. For example, the user may be required to press the 'Start' button a second time.

In step 535, the IMD safety control can determine if the IMD is still proximate to the microwave oven (i.e., a second detection for IMDs can be performed). Step 535 can be a fail-safe requiring the user to take action (i.e., ask the implantee to vacate the effective proximity); the user cannot simply ignore the alert and enter the acknowledgement without removing the IMD from the effective proximity.

When the IMD safety control determines that an IMD is still proximate to the microwave oven, method 500 can return to step 520 where the alert and notification can be reissued to the user. When the IMD safety control determines that the IMD is no longer proximate to the microwave oven, the IMD safety control can release the microwave oven into an enabled state in step 540.

It is important to note that the type of IMD safety control described in method 500 will not allow the microwave oven or other type of electronic device to operate until the IMD is no longer proximate. Thus, a person cooking microwave popcorn cannot inadvertently cause harm to a coworker having a pacemaker in the company break room.

Further, it should be emphasized that the operation of the IMD safety control should be tailored to address the specific situations that the type of electronic device is expected to encounter.

Figure 6:
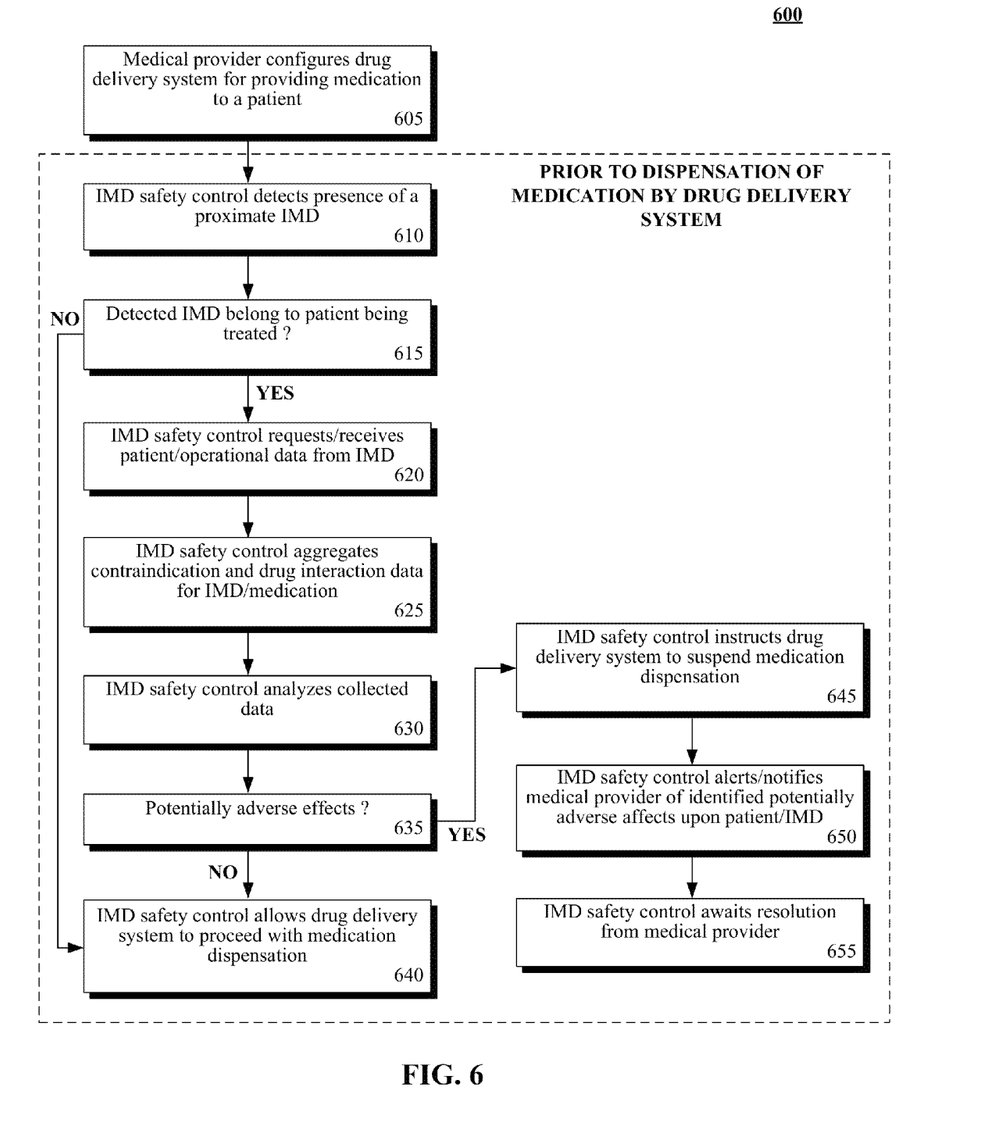
FIG. 6 is a flowchart of a method illustrating operation of a robust IMD safety control within a drug delivery system in accordance with an embodiment of the disclosure.

FIG. 6 is a flowchart of a method 600 illustrating operation of a robust IMD safety control within a drug delivery system in accordance with an embodiment of the disclosure. The method 600 can begin in step 605, where a medical provider can configure a drug delivery system for providing medication to a patient.

Prior to dispensation of the medication by the drug delivery system, the IMD safety control can detect the presence of a proximate IMD in step 610. In step 615, the IMD safety control can determine if the detected IMD belongs to the patient being treated. The determination performed in step 615 can require additional data exchanges between the IMD safety control and the IMD as well as between the IMD safety control and other data sources like a medical server housing patient data.

When the detected IMD does not belong to the patient being treated (i.e., the IMD is implanted within a staff or family member who is near the drug delivery system), method 600 can flow from step 615 to step 640 where the IMD safety control can allow the drug delivery system to proceed with dispensing medication to the patient. When the detected IMD belongs to the patient being treated, the IMD safety control can request and receive patient and/or operational data from the IMD in step 620.

In step 625, the IMD safety control can aggregate contraindication and drug interaction data for the IMD and/or the medication being dispensed. This data can be obtained from local and/or network data sources. The collected data can be analyzed by the IMD safety control in step 630.

In step 635, the IMD safety control can determine if the medication being dispensed can have a potentially adverse effect upon the patient and/or operation of the IMD. For example, the IMD safety control can obtain a list of medications that the patient is taking from the patient's medical record stored on the medical server as well as drug interaction information for the medication being dispensed. The IMD safety control can then determine if a harmful drug interaction has been overlooked and keep the medication from being automatically dispensed to the patient.

As another example, the IMD safety control would be able to determine if the medication being dispensed would adversely affect the effectiveness of or interact with the medication already provided by a patient's an insulin pump.

When the IMD safety control determines that the dispensed medication would not have a potentially adverse effect upon the patient and/or IMD, step 640 can be performed where the IMD safety control allows the drug delivery system to proceed with dispensing the medication. When it is determined that the dispensed medication can have a potentially adverse effect, the IMD safety control can instruct the drug delivery system to suspend medication dispensation in step 645.

In step 650, the IMD safety control can alert and/or notify the medical provider of the identified potentially adverse affects upon the patient and/or IMD. The IMD safety control can then await resolution from the medical provider in step 655.

It should be noted that the phrase "potentially adverse effects" does not have the same meaning as the phrase "possible side effects". A side effect can be a reaction of a drug with a person's physiology. A "potentially adverse effect", as used herein, can be an interaction between the function of the electronic device, drug delivery system in this example, and the patient or IMD that is widely accepted as disadvantageous.

For example, giving a diabetic patient insulin medication can cause side effects. Giving a diabetic patient having an implanted insulin pump insulin medication can have an adverse effect upon the patient's health.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed is:

1. A method for protecting an implanted medical device (IMD) from proximate device harmful interference comprising:

establishing a communication pathway between an implanted medical device (IMD) and a proximate electronic device, wherein the implanted medical device is an active implanted medical device having wireless communication capabilities, wherein performance of one or more functions by the proximate electronic device is known to have a potential to cause at least one adverse effect to a treatment provided by the implanted medical device or to an operation of the implanted medical device when the implanted medical device is within an effective proximity of the electronic device at a time the electronic device performs the one or more functions, wherein the communication pathway for wireless communication refers to any communication medium not requiring a dedicated physical wire between communication endpoints over which an information bearing signal is conveyed;

the implanted medical device wirelessly conveying a message over the communication pathway to the electronic device indicating an existence of the implanted medical device (IMD) within wireless communication range of the electronic device and indicating a safety requirement or operational data specific to the implanted medical device, wherein the wireless communication range corresponds to at least a high likelihood of the implanted medical device being within the effective proximity of the proximate electric device; and the conveyance of the message from the implanted medical device placing the proximate electronic device, which receives the message, on notice, such that the electronic device responsive to being on notice is able to minimize potential harmful effects of performing the one or more functions while the implanted medical device is within the effective proximity, is able to alert a user of the electronic device of potential harmful effects of performing the one or more functions while the implanted medical device is within the effective proximity, or automatically disable the one or more functions while the implanted medical device is in the effective proximity, wherein the implanted medical device is a man-made device that is partially or totally inserted into a human body or a natural orifice of the human body, where the implanted medical device is operationally designed to remain in place after being inserted for over thirty days.

2. The method of claim 1, further comprising:
the implanted medical device conveying a notification or an alert to a wearer of the implanted medical device or to other humans within the effective proximity of a presence of the electronic device having the one or more functions able to cause the at least one adverse effect on the implanted medical device.

3. The method of claim 1, further comprising:
the implanted medical device changing operational state from a default while near the effective proximity to minimize harm resulting from the one or more electronic device executing the one or more functions; and
the implanted medical device changing operational state back to the default when the implanted medical device is no longer near the effective proximity.

4. The method of claim 1, further comprising:
exchanging communications between the implanted medical device and the electronic device as the electronic device performs the one or more functions; and
dynamically altering optional state of the implanted medical device responsive to the exchanged communications to minimize or eliminate the adverse effect.

5. The method of claim 1, further comprising:
the implanted medical device detecting one of more adverse effects from the one or more functions; and
responsive to the detecting, the implanted medical device establishing the communication pathway and wirelessly conveying the message over the communication pathway.

6. The method of claim 1, wherein the implanted medical device utilizes at least one of a near field communication (NFC) transmission, a BLUETOOTH transmission having a range of less than twenty meters, and a radio transmission having a range of less than twenty meters to wirelessly convey the message.

7. The method of claim 1, wherein the implanted medical device utilizes at least one of a near field communication (NFC) transmission, a BLUETOOTH transmission, and a radio transmission to wirelessly conveying the message, wherein the NFC transmission, the BLUETOOTH transmission, or the radio transmission has a range of less than one meter.

8. The method of claim 1, wherein the electronic device is one of a mobile telephony device, a touch-screen computing device, a personal computer, a microwave device, and a medical device.

9. The method of claim 1, wherein the implanted medical device is one of a neurostimulator, a cardioverter-defibrillator, a cardiac resynchronization device, a pacemaker, and a medical pump.

10. An implanted medical device (IMD) comprising:
one or more processors;
a wireless transmitter;
a non-transitory storage medium storing programmatic instructions, wherein execution of the programmatic instructions by the one or more processors causes the implanted medical device to:
(a) establish a communication pathway between the implanted medical device (IMD) and a proximate electronic device, wherein the implanted medical device is an active implanted medical device having wireless communication capabilities via the wireless transmitter, wherein performance of one or more functions by the proximate electronic device is known to have a potential to cause at least one adverse effect to a treatment provided by the implanted medical device or to an operation of the implanted medical device when the implanted medical device is within an effective proximity of the proximate electronic device at a time the proximate electronic device performs the one or more functions, wherein the communication pathway for wireless communication refers to any communication medium not requiring a dedicated physical wire between communication endpoints over which an information bearing signal is conveyed, wherein the wireless transmitter refers to any transmitter for conveying the information bearing signal over the communication pathway; and
(b) wirelessly convey a message over the communication pathway to the electronic device indicating an existence of the implanted medical device (IMD) within wireless communication range of the proximate electronic device and indicating a safety requirement or operational data specific to the implanted medical device, wherein the wireless communication range corresponds to at least a high likelihood of the implanted medical device being within the effective proximity of the proximate electric device,
wherein the conveyance of the message from the implanted medical device places the proximate electronic device, which receives the message, on notice, such that the proximate electronic device responsive to being on notice is able to minimize potential harmful effects of performing the one or more functions while the implanted medical device is within the effective proximity, is able to alert a user of the proximate electronic device of potential harmful effects of performing the one or more functions while the implanted medical device is within the effective proximity, or automatically disable the one or more functions while the implanted medical device is in the effective proximity, wherein the implanted medical device is a man-made device that is partially or totally inserted into a human body or a natural orifice of the human body, where the implanted medical device is operationally designed to remain in place after being inserted for over thirty days.

11. The system of claim 10, wherein execution of the programmatic instructions by the one or more processors causes the implanted medical device to:
convey a notification or an alert to a wearer of the implanted medical device or to other humans within the effective proximity of a presence of the proximate electronic device having the one or more functions able to have cause the at least one adverse effect on the implanted medical device.

12. The system of claim 10, wherein execution of the programmatic instructions by the one or more processors causes the implanted medical device to:
change operational state from a default while near the effective proximity to minimize harm resulting from the proximate electronic device executing the one or more functions; and
change operational state back to the default when the implanted medical device is no longer near the effective proximity.

13. The system of claim 10, wherein execution of the programmatic instructions by the one or more processors causes the implanted medical device to:
exchange communications between the implanted medical device and the proximate electronic device as the proximate electronic device performs the one or more functions; and
dynamically alter optional state of the implanted medical device responsive to the exchanged communications to minimize or eliminate the adverse effect.

14. The system of claim 10, wherein execution of the programmatic instructions by the one or more processors causes the implanted medical device to:
detect one of more adverse effects from the one or more functions; and
responsive to the detecting, establish the communication pathway and wirelessly conveying the message over the communication pathway.

15. The system of claim 10, wherein the proximate electronic device is one of a mobile telephony device, a touchscreen computing device, a personal computer, a microwave device, and a medical device.

16. The system of claim 10, wherein the implanted medical device is one of a neurostimulator, a cardioverter-defibrillator, a cardiac resynchronization device, a pacemaker, and a medical pump.

17. The system of claim 10, wherein the implanted medical device is a neurostimulator, wherein execution of the programmatic instructions by the one or more processors causes the neurostimulator to:
change operational state from a default while near the effective proximity to minimize harm resulting from the proximate electronic device executing the one or more functions; and
change operational state back to the default when the implanted medical device is no longer near the effective proximity.

18. The system of claim 10, wherein the implanted medical device is a cardioverter-defibrillator, wherein execution of the programmatic instructions by the one or more processors causes the cardioverter-defibrillator to:
change operational state from a default while near the effective proximity to minimize harm resulting from the proximate electronic device executing the one or more functions; and
change operational state back to the default when the implanted medical device is no longer near the effective proximity.

19. The system of claim 10, wherein the implanted medical device is a cardiac resynchronization device, wherein execution of the programmatic instructions by the one or more processors causes the cardiac resynchronization device to:
change operational state from a default while near the effective proximity to minimize harm resulting from the proximate electronic device executing the one or more functions; and
change operational state back to the default when the implanted medical device is no longer near the effective proximity.

20. The system of claim 10, wherein the implanted medical device is a pacemaker, wherein execution of the programmatic instructions by the one or more processors causes the pacemaker to:
change operational state from a default while near the effective proximity to minimize harm resulting from the proximate electronic device executing the one or more functions; and
change operational state back to the default when the implanted medical device is no longer near the effective proximity.

21. The system of claim 10, wherein the implanted medical device is a medical pump, wherein execution of the programmatic instructions by the one or more processors causes the medical pump to:
change operational state from a default while near the effective proximity to minimize harm resulting from the proximate electronic device executing the one or more functions; and
change operational state back to the default when the implanted medical device is no longer near the effective proximity.

22. The system of claim 10, wherein the implanted medical device is a bone fusion stimulator, wherein execution of the programmatic instructions by the one or more processors causes the bone fusion stimulator to:
change operational state from a default while near the effective proximity to minimize harm resulting from the proximate electronic device executing the one or more functions; and
change operational state back to the default when the implanted medical device is no longer near the effective proximity.

23. The system of claim 10, wherein the implanted medical device is a cochlear implant, wherein execution of the programmatic instructions by the one or more processors causes the cochlear implant to:
change operational state from a default while near the effective proximity to minimize harm resulting from the proximate electronic device executing the one or more functions; and
change operational state back to the default when the implanted medical device is no longer near the effective proximity.

24. The system of claim 10, wherein the implanted medical device is a gastric stimulator, wherein execution of the programmatic instructions by the one or more processors causes the gastric stimulator to:

change operational state from a default while near the effective proximity to minimize harm resulting from the proximate electronic device executing the one or more functions; and change operational state back to the default when the implanted medical device is no longer near the effective proximity.

25. A computer program product comprising a non-transitory computer readable storage medium having computer usable program code embodied therewith, the computer usable program code comprising:

computer usable program code configured to establishing a communication pathway between an implanted medical device (IMD) and a proximate electronic device, wherein the implanted medical device is an active implanted medical device having wireless communication capabilities, wherein performance of one or more functions by the proximate electronic device is known to have a potential to cause at least one adverse effect to a treatment provided by the implanted medical device or to an operation of the implanted medical device when the implanted medical device is within an effective proximity of the proximate electronic device at a time the proximate electronic device performs the one or more functions, wherein the communication pathway for wireless communication refers to any communication medium not requiring a dedicated physical wire between communication endpoints over which an information bearing signal is conveyed; and computer usable program code configured to wirelessly conveying a message over the communication pathway from the implanted medical device to the electronic device indicating an existence of the implanted medical device (IMD) within wireless communication range of the proximate electronic device and indicating a safety requirement or operational data specific to the implanted medical device, wherein the wireless communication range corresponds to at least a high likelihood of the implanted medical device being within the effective proximity of the proximate electric device, wherein the conveyance of the message from the implanted medical device places the proximate electronic device, which receives the message, on notice, such that the proximate electronic device responsive to being on notice is able to minimize potential harmful effects of performing the one or more functions while the implanted medical device is within the effective proximity, is able to alert a user of the proximate electronic device of potential harmful effects of performing the one or more functions while the implanted medical device is within the effective proximity, or automatically disable the one or more functions while the implanted medical device is in the effective proximity, wherein the implanted medical device is a man-made device that is partially or totally inserted into a human body or a natural orifice of the human body, where the implanted medical device is operationally designed to remain in place after being inserted for over thirty days.

26. The computer program product of claim 25, further comprising:

computer usable program code configured to conveying a notification or present an alert to a wearer of the implanted medical device or to other humans within the effective proximity of a presence of the proximate electronic device having the one or more functions able to have cause the at least one adverse effect on the implanted medical device.

27. The computer program product of claim 25, further comprising:

computer usable program code configured to change an operational state of the implanted medical device from a default while near the effective proximity to minimize harm resulting from the proximate electronic device executing the one or more functions; and computer usable program code configured to change an operational state of the implanted medical device back to the default when the implanted medical device is no longer near the effective proximity.

28. The computer program product of claim 25, further comprising:

computer usable program code configured to detect at the implanted medical device one of more adverse effects from the one or more functions; and computer usable program code configured to, responsive to the detecting, establish the communication pathway and wirelessly conveying the message over the communication pathway.

* * * * *